United States Patent
Amir et al.

(10) Patent No.: US 6,578,962 B1
(45) Date of Patent: Jun. 17, 2003

(54) CALIBRATION-FREE EYE GAZE TRACKING

(75) Inventors: Arnon Amir, Cupertino, CA (US); Myron Dale Flickner, San Jose, CA (US); David Bruce Koons, San Jose, CA (US); Gregory Fraser Russell, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 43 days.

(21) Appl. No.: 09/844,682

(22) Filed: Apr. 27, 2001

(51) Int. Cl.[7] .............................. A61B 3/14; G09G 5/08
(52) U.S. Cl. ...................................... 351/209; 345/157
(58) Field of Search .............................. 351/209, 210, 351/208, 200, 246, 206, 205, 211, 221; 396/51; 345/156, 157, 158, 973

(56) References Cited

U.S. PATENT DOCUMENTS

| | | | |
|---|---|---|---|
| 4,568,159 A | 2/1986 | Baldwin | 351/210 |
| 4,595,990 A | 6/1986 | Garwin et al. | 364/518 |
| 4,597,648 A | 7/1986 | Feldon et al. | 351/212 |
| 4,836,670 A | 6/1989 | Hutchinson | 351/210 |
| 4,950,069 A | 8/1990 | Hutchinson | 351/210 |
| 4,973,149 A | 11/1990 | Hutchinson | 351/210 |
| 5,016,282 A | 5/1991 | Tomono et al. | 382/2 |
| 5,231,674 A * | 7/1993 | Cleveland et al. | 351/210 |
| 5,325,133 A * | 6/1994 | Adachi | 351/209 |
| 5,471,542 A * | 11/1995 | Ragland | 351/208 |
| 5,861,940 A | 1/1999 | Robinson et al. | 351/221 |
| 6,152,563 A * | 11/2000 | Hutchinson et al. | 351/209 |
| 6,204,828 B1 | 3/2001 | Amir et al. | 345/7 |
| 6,421,064 B1 * | 7/2002 | Lemelson et al. | 351/208 |

FOREIGN PATENT DOCUMENTS

| | | | |
|---|---|---|---|
| WO | WO 9909880 | 8/1997 | A61B/3/113 |
| WO | WO 0133323 | 10/1999 | G06F/3/00 |

OTHER PUBLICATIONS

K. Talmi and J. Liu, "Eye and Gaze Tracking for Visually Controlled Interactive Stereoscopic Displays", Image Communication, vol. 14, No. 10, p. 799–810, 1999.

(List continued on next page.)

*Primary Examiner*—Marvin M. Lateef
*Assistant Examiner*—John R. Sanders
(74) *Attorney, Agent, or Firm*—Marc D. McSwain

(57) ABSTRACT

A system and method for calibration-free tracking of a user's eye gaze vector and point of regard even if substantial head movement or rotation occurs. The preferred embodiment includes two synchronized interlaced cameras, each viewing the user's eye and having on-axis lighting that is alternately modulated. An image difference between lighted and unlighted images of the eye is used to identify a user's pupil. A plane containing the gaze vector is defined by rotating a base plane through the angle in a camera image plane between a pupil center, a first glint, and a second glint. The intersection of two such planes (one from each camera), defines the gaze vector. The gaze position is the intersection of the gaze vector with the object being viewed by the user. Alternate embodiments are also described.

30 Claims, 14 Drawing Sheets

OTHER PUBLICATIONS

S. Shih, Y. Wu, J. Liu, "A Calibration–Free Gaze Tracking Technique", ICPR 2000, vol. 4, pp. 201–204, 2000.

J. Liu et al., "Three–dimensional PC: toward novel forms of human–computer interaction", in Three–Dimensional Video and Display: Devices and Systems SPIE CR76, Nov. 5–8, 2000, Boston, MA, USA.

K. White, Jr. et al., "Spatially Dynamic Calibration of an Eye–Tracking System", IEEE Transactions on Systems, Man and Cybernetics, vol. 23, No. 4, Jul./Aug. 1993, p. 1162–1168.

Y. Ebisawa et al., "Effectiveness of Pupil Area Detection Technique Using Two Light Sources and Image Difference Method", Proceedings of the 15th Annual International Conference of IEEE Engineering in Medicine and Biology Society, vol. 15, Oct. 1993, p. 1268–1269.

Technical Report MSR–TR–98–71 from http://research.microsoft.com/~zhang/Papers/TR98–71.pdf also available as: Z. Zhang, "A Flexible New Technique for Camera Calibration", IEEE Transactions on Pattern Analysis and Machine Intelligence, 22(11):1330–1334, 2000.

German Patent Application DE19810728A1 "Eye Movement Detection and Processing Device", published Sep. 30, 1999 by S. Astoor and J. Liu, A61B3/113.

* cited by examiner

CALIBRATION-FREE EYE GAZE TRACKING

FIELD OF THE INVENTION

This invention relates to the determination of a user's eye gaze vector and point of regard by analysis of images taken of a user's eye. The invention relates more specifically to eye gaze tracking without the need to calibrate for specific users' eye geometries and to subsequently recalibrate for user head position.

BACKGROUND OF THE INVENTION

Eye gaze tracking technology has proven to be useful in many different fields, including human-computer interfaces for assisting disabled people interact with a computer. The eye gaze tracker can be used as a mouse emulator for a personal computer, for example, helping disabled people to move a cursor on a display screen to control their environment and communicate messages. Gaze tracking can also be used for industrial control, aviation, and emergency room situations where both hands are needed for tasks other than operation of a computer but where an available computer is useful. There is also significant research interest in eye gaze tracking for babies and animals to better understand such subjects' behavior and visual processes. Commercial eye gaze tracking systems are made by ISCAN Incorporated (Burlington Mass.), LC Technologies (Fairfax Va.), and Applied Science Laboratories (Bedford Mass.).

There are many different schemes for detecting both the direction in which a user is looking and the point upon which the user's vision is fixated. Any particular eye gaze tracking technology should be relatively inexpensive, reliable, unobtrusive, easily learned and used and generally operator-friendly to be widely accepted. The corneal reflection method of eye gaze tracking is increasing in popularity, and is well-described in the following U.S. patents, which are hereby incorporated by reference: 4,595,990, 4,836,670, 4,950,069, 4,973,149, 5,016,282, 5,231,674, 5,471,542, 5,861,940, 6,204,828. These two articles also describe corneal reflection eye gaze tracking and are also hereby incorporated by reference: "Spatially Dynamic Calibration of an Eye-Tracking System", K. White, Jr. et al., IEEE Transactions on Systems, Man, and Cybernetics, vol. 23, no. 4, July/August 1993, p. 1162–1168, referred to hereafter as White, and "Effectiveness of Pupil Area Detection Technique", Y. Ebisawa et al., Proceedings of the $15^{th}$ Annual International Conference of IEEE Engineering in Medicine and Biology Society, vol. 15, October 1993, p. 1268–1269.

Corneal reflection eye gaze tracking systems project light toward the eye and monitor the angular difference between pupil position and the reflection of the light beam. Near-infrared light is often employed, as users cannot see this light and are therefore not distracted by it. Usually only one eye is monitored, and it isn't critical which eye is monitored. The light reflected from the eye has two major components. The first component is a 'glint', which is a very small and very bright virtual image of the light source reflected from the front surface of the corneal bulge of the eye. The glint position remains relatively fixed in an observer's image field as long as the user's head remains stationary and the corneal sphere rotates around a fixed point. The second component is light that has entered the eye and has been reflected back out from the retina. This light serves to illuminate the pupil of the eye from behind, causing the pupil to appear as a bright disk against a darker background. This retroreflection, or "bright eye" effect familiar to flash photographers, provides a very high contrast image. Unlike the glint, the pupil center's position in the image field moves significantly as the eye rotates. An oculometer determines the center of the pupil and the glint, and the change in the distance and direction between the two as the eye is rotated. The orientation of the eyeball can be inferred from the differential motion of the pupil center relative to the glint. The eye is often modeled as a sphere of about 13.3 mm radius having a spherical corneal bulge of about 8 mm radius; the eyes of different users will have variations from these typical values, but individual dimensional values do not generally vary significantly in the short term.

As shown in prior art FIG. 1, the main components of a corneal reflection eye gaze tracking system include a video camera sensitive to near-infrared light, a near-infrared light source (often a light-emitting diode) typically mounted to shine along the optical axis of the camera, and a computer system for analyzing images captured by the camera. The on-axis light source is positioned at or near the focal center of the camera. Image processing techniques such as intensity thresholding and edge detection identify the glint and the pupil from the image captured by the camera using on-axis light, and locate the pupil center in the camera's field of view as shown in prior art FIG. 2.

Human eyes do not have equal resolution over the entire field of view, nor is the portion of the retina providing the most distinct vision located precisely on the optical axis. The eye directs its gaze with great accuracy because the photoreceptors of the human retina are not uniformly distributed but instead show a pronounced density peak in a small region known as the fovea centralis. In this region, which subtends a visual angle of about one degree, the receptor density increases to about ten times the average density. The nervous system thus attempts to keep the image of the region of current interest centered accurately on the fovea as this gives the highest visual acuity. A distinction is made between the optical axis of the user's eye versus the foveal axis along which the most acute vision is achieved. As shown in prior art FIG. 3, the optical axis is a line going from the center of the spherical corneal bulge through the center of the pupil. The optical axis and foveal axis are offset in each eye by an inward horizontal angle of about five degrees, with a variation of about one and one half degrees in the population. The offsets of the foveal axes with respect to the optical axes of a user's eyes enable better stereoscopic vision of nearby objects. The offsets vary from one individual to the next, but individual offsets do not vary significantly in the short term. For this application, the gaze vector is defined as the optical axis of the eye. The gaze position or point of regard is defined as the intersection point of the gaze vector with the object being viewed (e.g. a point on a display screen some distance from the eye). Adjustments for the foveal axis offsets are typically made after determination of the gaze vector; a default offset angle value may be used unless values from a one-time measurement of a particular user's offset angles are available.

Unfortunately, calibration is required for all existing eye gaze tracking systems to establish the parameters describing the mapping of camera image coordinates to display screen coordinates. Different calibration and gaze direction calculation methods may be categorized by the actual physical measures they require. Some eye gaze tracking systems use implicit models that map directly from pupil and glint positions in the camera's image plane to the point of regard in screen coordinates. Other systems use physically-based explicit models that take into account eyeball radius, radius of curvature of the cornea, offset angle between the optical axis and the foveal axis, head and eye position in space, and distance between the center of the eyeball and the center of the pupil as measured for a particular user. During calibration, the user may be asked to fix his or her gaze upon certain "known" points in a display. At each coordinate location, a sample of corresponding gaze vectors is computed and used to adapt the system to the specific properties of the user's eye, reducing the error in the estimate of the gaze vector to an acceptable level for subsequent operation. The user may also be asked to click a mouse button after visually fixating on a target, but this approach may add synchronization problems, i.e. the user could look away from the target and then click the mouse button. Also, with this approach the system would get only one mouse click for each target, so there would be no chance to average out involuntary eye movements. Alternately, during calibration, the user may visually track a moving calibration icon on a display that traverses a discrete set of known screen coordinates. Calibration may need to be performed on a per-user or per-tracking-session basis, depending on the precision and repeatability of the tracking system.

prior art eye gaze tracking systems also require subsequent recalibration to accurately adjust for head motion. U.S. Pat. No. 5,016,282 teaches the use of three reference points on calibration glasses to create a model of the head and determine the position and orientation of the head for the eye gaze tracking system. However, it is not likely that users will generally be willing to wear special glasses merely to enable the system to account for head motion in everyday use. Other commercial eye gaze tracking systems are head mounted, and therefore have no relative head motion difficulties to resolve. However, these systems are mainly designed for military or virtual reality applications wherein the user typically also wears a head mounted display device coupled to the eye gaze tracking device. Head mounted displays are inconvenient and not generally suitable for long periods of computer work in office and home environments. Details of camera calibration and conversion of measured two-dimensional points in the image plane to three-dimensional coordinates in real space are described in "A Flexible New Technique for Camera Calibration", Z. Zhang, IEEE Transactions on Pattern Analysis and Machine Intelligence, 22(11): 1330–1334, 2000, (also available as Technical Report MSR-TR-98-71 at http://research.microsofl.com/~zhang/Papers/TR98-71.pdf), which is hereby incorporated by reference.

White offers an improvement in remote eye gaze tracking in the presence of lateral head translations (e.g. parallel to a display screen) of up to 20 cm. White uses a second light source to passively recalibrate the system. The second light source creates a second glint. White claims that a single initial static (no head motion) calibration can be dynamically adjusted as the head moves, leading to improved accuracy under an expanded range of head motions without a significantly increased system cost. Unfortunately, White's system compensates only for lateral head displacements, i.e. not for motion to/from the gaze position, and not for rotation. Rotation of a user's head is particularly troublesome for prior art gaze tracking systems as it changes the distance from the eye to both the object under observation and to the camera generating images of the eye.

While the aforementioned prior art methods are useful advances in the field of eye gaze tracking, systems that do not require calibration would increase user convenience and broaden the acceptance of eye gaze tracking technology. A system for providing eye gaze tracking requiring little or no knowledge of individual users' eye geometries, and requiring no subsequent calibration for head movement is therefore needed.

SUMMARY OF THE INVENTION

It is accordingly an object of this invention to devise a system and method for eye gaze tracking wherein calibration for individual users' eye geometries is not required.

It is a related object of the invention to devise a system and method for eye gaze tracking wherein subsequent recalibration for head movement is not required.

It is a related object of the invention to determine a gaze vector and to compute a point of regard as the intersection of the gaze vector and an observed object.

It is a related object of the preferred embodiment of the invention that two cameras each having a co-located and co-oriented light source are used to capture images of a user's eye. It is a related object of the preferred embodiment of the invention to capture images of a user's eye such that the pupil center in each image and glints generated by each light source may be readily identified and located in the image plane of each camera.

It is a related object of the preferred embodiment of the invention to compute a first angle between three points in the image plane of the first camera, specifically the angle between the pupil center, the first glint (generated by the first camera's light source) and the second glint (generated by the second camera's light source). Similarly, it is a related object of the preferred embodiment of the invention to compute a second angle between three points in the image plane of the second camera, specifically the angle between the pupil center, the second glint and the first glint.

It is a related object of the preferred embodiment to define a base plane spanning the first camera's focal center, the second camera's focal center, and the common point in space (on the eye) at which light from one camera's light source reflects to the other camera. It is a related object of the preferred embodiment of the invention to define a first plane by rotating the base plane by the first angle about a line from the focal center of the first camera and the first glint in the first camera's image plane. The intersection of the first plane with the display screen plane defines a first line containing the point of regard. Similarly, it is a related object of the preferred embodiment of the invention to define a second plane by rotating the base plane by the second angle about a line from the focal center of the second camera and the second glint in the second camera's image plane. The intersection of the second plane with the display screen plane defines a second line containing the point of regard.

It is a related object of the preferred embodiment of the invention to compute the gaze vector as a line defined by the intersection between the first plane and the second plane and extending from the user's eye toward an observed object. The point of regard is computed from the intersection of the gaze vector with the observed object, which corresponds to the intersection of the first line and the second line when the observed object is planar. Correction for foveal axis offsets may be added.

It is a related object of the second embodiment that each of the two cameras require only light originally emitted by its own on-axis light source. It is a related object of the second embodiment of the invention to compute a first plane including a first glint position in the first camera's image plane, a pupil center position in the first camera's image plane, and the focal center of the first camera. Similarly, it is a related object of the second embodiment of the invention to compute a second plane including a second glint position in the second camera's image plane, a pupil center in the second camera's image plane, and the focal center of the second camera. The intersection of the first plane with the display screen plane defines a first line containing the point of regard. The intersection of the second plane with the display screen plane defines a second line containing the point of regard. The gaze vector is a line defined by the intersection between the first plane and the second plane and extending from the user's eye toward an observed object. The point of regard is computed from the intersection of the gaze vector with the observed object, which corresponds to the intersection of the first line and the second line when the observed object is planar.

It is a related object of the third embodiment of the invention to use a single camera having a co-located and co-oriented light source to capture images of a user's eye including glints and a pupil center. It is a related object of the third embodiment of the invention to determine the distance in the camera's image plane between the pupil center and the glint. Using an estimated distance between the user's eye and an observed object, and a one-time measurement of the user's corneal curvature, the gaze vector and point of regard are determined.

The foregoing objects are believed to be satisfied by the embodiments of the present invention as described below.

DETAILED DESCRIPTION

Figure 1:
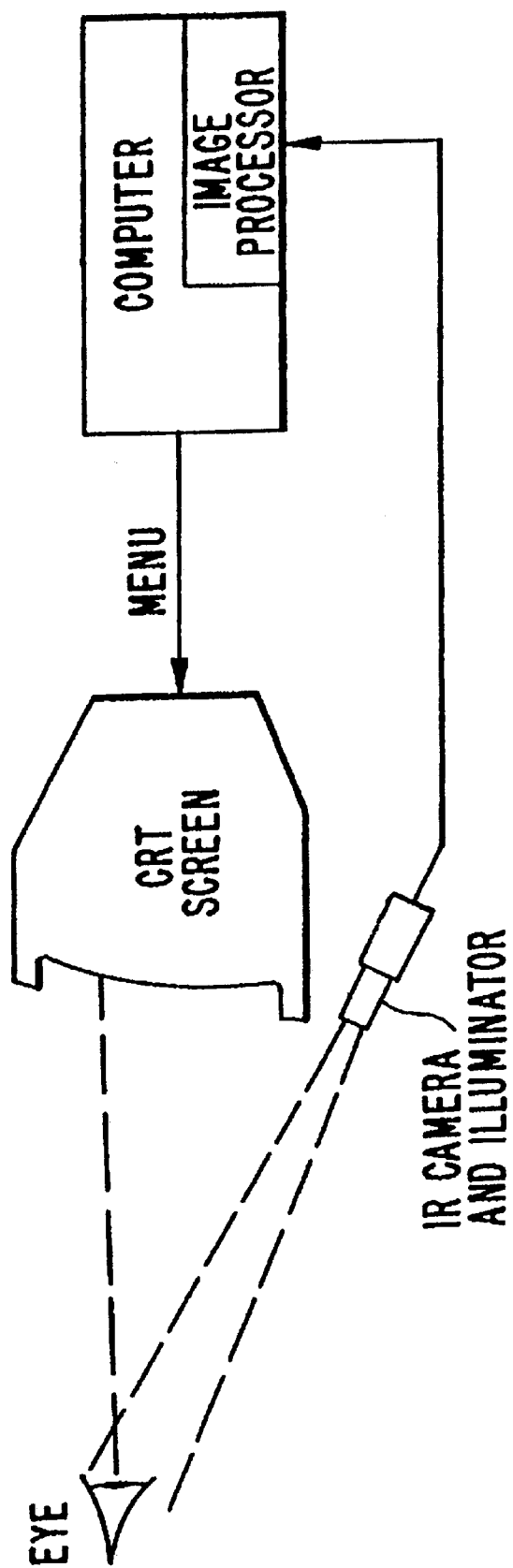
FIG. 1 is a prior art diagram of an eye gaze tracking system.
Figure 2:
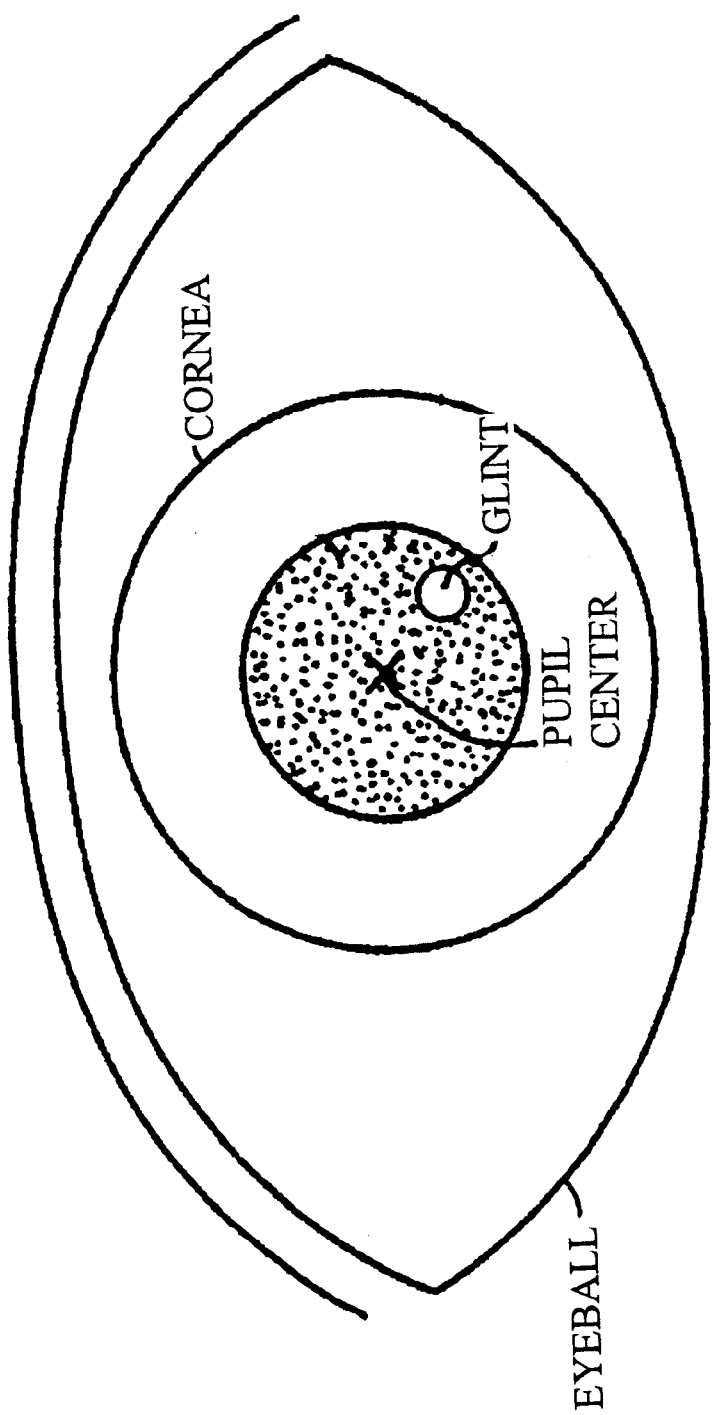
FIG. 2 is a prior art diagram of a user's eye as viewed by a camera.
Figure 3:
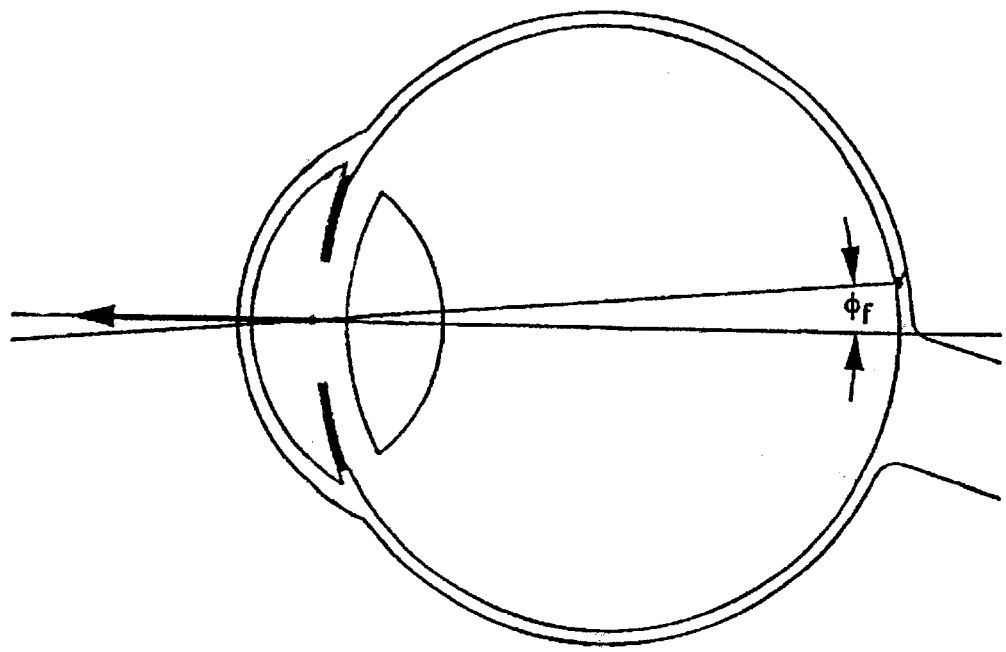
FIG. 3 is a prior art diagram of the foveal and optical axes and their offset angle.
Figure 3:
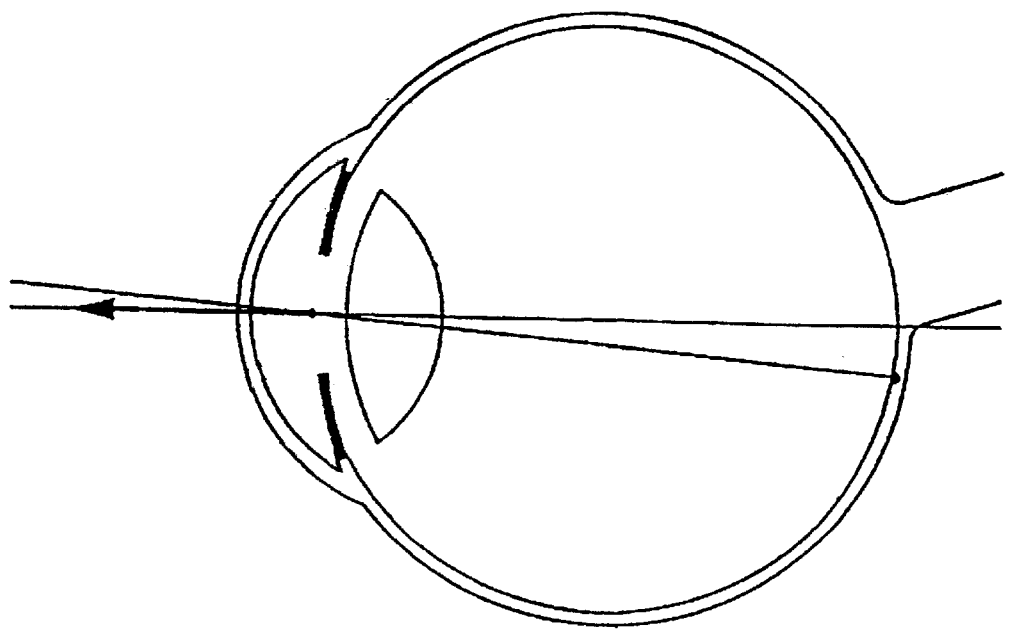
Figure 4:
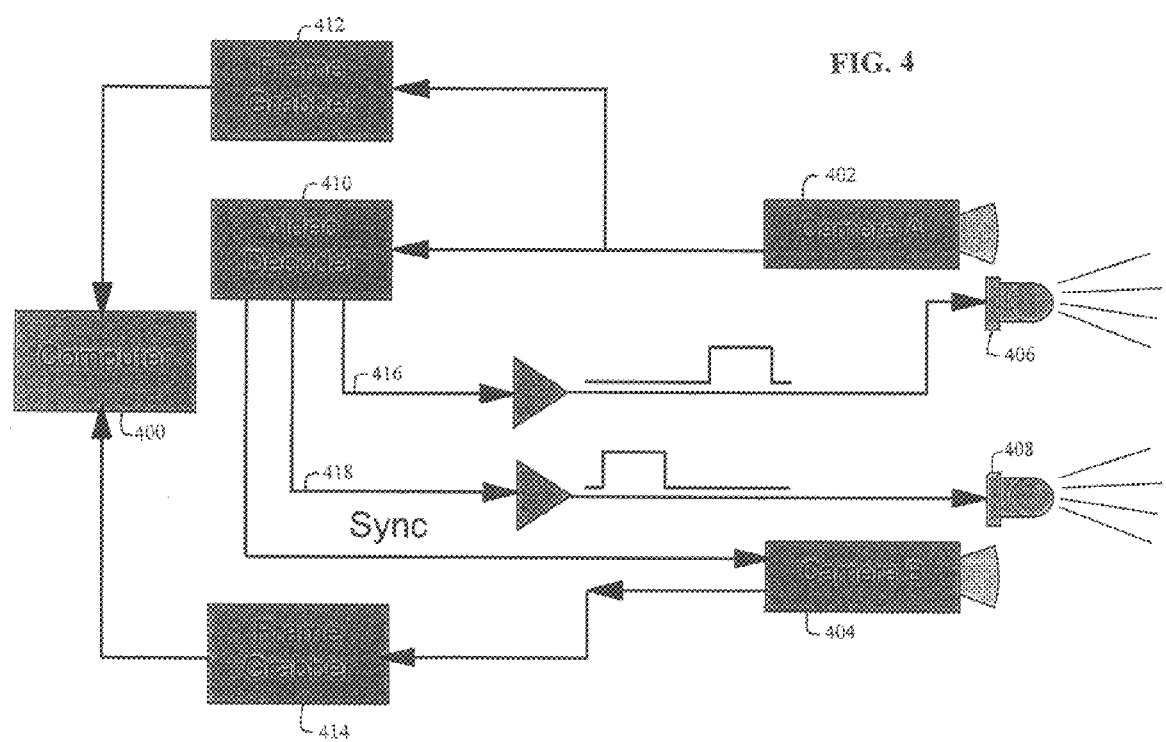
FIG. 4 is a diagram of the system of the preferred embodiment of the present invention.

Referring now to FIG. 4, a diagram of the system of the preferred embodiment of the present invention is shown. The system preferably includes a computer 400, a first camera 402, a second camera 404, a first light source 406, a second light source 408, a video decoder 410, a first frame grabber 412, and a second frame grabber 414. First camera 402 and second camera 404 are each video cameras, spaced apart, generating respective video signals representing repeating interlaced scans of a respective image field. In a conventional interlaced video camera, odd-numbered raster rows are typically scanned from left to right and then top to bottom, and then even-numbered raster rows are scanned in the same manner during each repetition. Vertical and horizontal synchronization signals from first camera 402 are fed into video decoder 410, which passes the synchronization signals to second camera 404, which responsively scans its image field in time with the scans of first camera 402. Alternately, each of the cameras could be driven by synchronization signals originating from computer 400, video decoder 410, or from another signal source. Both cameras are aimed at and focused upon one of the user's eyes and is equipped with tracking mechanisms (not shown), well known to those of ordinary skill in the art, that actively keep the cameras aimed at the user's eye. These tracking mechanisms sometimes operate by rapidly adjusting the orientation of each camera to keep the brightest portion of the image centered in its respective field of view. Note that in the preferred embodiment no fixed rotational reference for either camera is required, i.e. either camera could be rolled about its optical axis without causing difficulties.

First light source 406 and second light source 408 are preferably light-emitting diodes (LEDs) that produce light of near-infrared wavelengths when energized. First light source 406 is positioned to emit light substantially along the optical axis of first camera 402 in the direction of its field of view. Second light source 408 is similarly positioned to emit light substantially along the optical axis of second camera 404 in the direction of its field of view. The brightness of each light source, when energized, is adjusted to keep the image brightness in the eye area of each camera's field of view substantially the same. The duty cycle of each light source can be adjusted downward to enable production of pulses of brighter light intensity.

One method of acquiring a clearly defined and easy to process pupil image is to generate a difference image by effectively subtracting an unlit image of the eye from a lit image of the eye. In the preferred embodiment, video decoder 410 generates an even field control signal 416 whenever even-numbered raster rows are being scanned by the cameras, and generates an odd field control signal 418 whenever odd-numbered raster rows are being scanned by the cameras. Even field control signal 416 triggers the illumination of first light source 406, and odd field control signal 418 triggers the illumination of second light source 408. The two light sources are thus alternately energized during each alternately interlaced camera scan. The result is that each camera produces images composed of two fields, each illuminated by a different light source, one on-axis and the other off-axis. Images from the cameras are captured by first frame grabber 412 and second frame grabber 414, digitized, and then forwarded to computer 400 for subsequent processing. Subtracting the rows exposed by off-axis light from the corresponding row exposed by the on-axis light in images from first camera 402 produces a difference image that very clearly identifies the pupil as seen by first camera 402. A similar subtraction performed on images from second camera 404 produces a difference image that very clearly identifies the pupil as seen by second camera 404, as described in U.S. Pat. No. 5,016,282. Alternate lighting is not an essential aspect of the invention but works particularly well.

The relative positions and orientations of first camera 402, second camera 404, and the object being viewed by the user (e.g. a display screen) are known from a one-time user-independent calibration of the system of the present invention performed when the system components are first deployed. Attachment of the cameras to the display screen at known points would simplify the initial calibration, but cameras need not be positioned on the display screen or in the plane of the display screen. Similarly, the optical parameters of both cameras (e.g. focal length) and the size of the display screen are assumed to be known, and the user's cornea is assumed to be rotationally symmetric about the optical axis.

Figure 5:
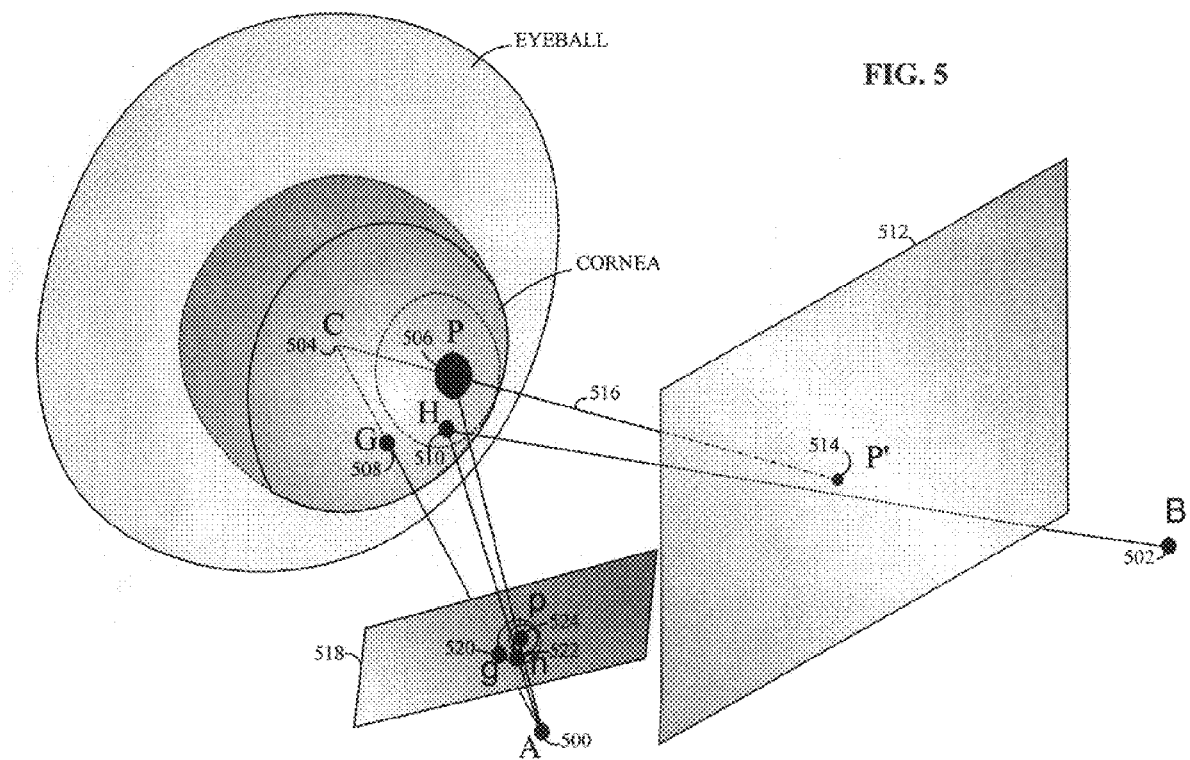
FIG. 5 is a diagram of the user's eye according to the preferred embodiment of the present invention.

Referring now to FIG. 5, a diagram of a user's eye is shown in accordance with the preferred embodiment of the present invention. Point A is the position of first focal center 500 of first camera 402 and the position of first light source 406. A pinhole camera model is used with a perspective projection to the image plane. Light from first light source 406 reflects from the user's cornea at point G back to first camera 402, producing a first glint 508 in the image from first camera 402. Point B is the position of second focal center 502 of second camera 404 and the position of second light source 408. Light emitted from an off-axis light source (e.g. second light source 408) reflects from the user's cornea at point H and is visible by first camera 402 as second glint 510. Identification of which glint is due to which light source is simplified by use of alternate lighting during image capture as described above. Point C is the center of curvature 504 of the corneal bulge (note, the corneal bulge is usually modeled as spherical but of course in reality the corneal bulge is not a complete sphere within the eyeball). Point P is pupil center 506. Points G and H lie on plane ABC. Point P' is the point of regard 514 on display screen 512, i.e. the intersection point between line CP (which is the optical axis and gaze vector 516) and display screen 512 plane. Image plane 518 is a plane orthogonal to the optical axis of first camera 402 (for clarity, image plane 518 is shown in front of first focal center 500, but in reality image plane 518 will be behind first focal center 500 and points on image plane 518 will be projections). Point g 520 is the image of (on-axis) first glint 508 in image plane 518. Point h 522 is the image of (off-axis) second glint 510 in image plane 518. Point p 524 is the image of pupil center 506 in image plane 518.

Figure 6:
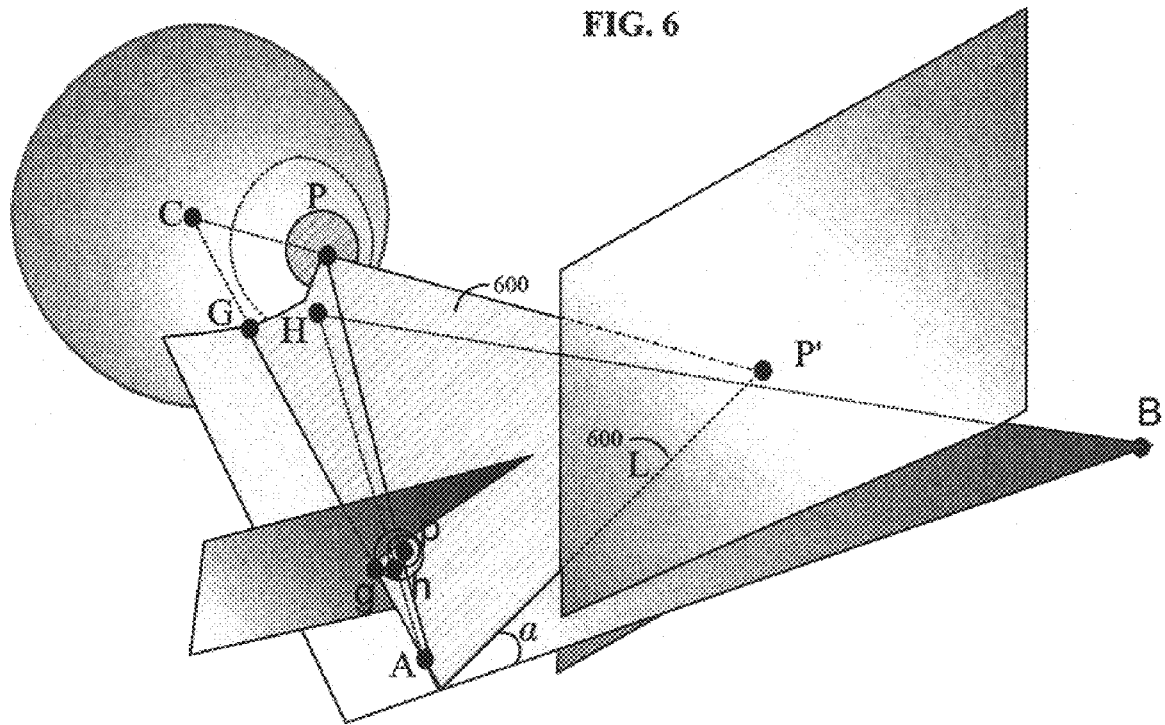
FIG. 6 is a diagram of the user's eye including a first plane Agp containing the gaze vector according to the preferred embodiment of the present invention.

Referring now to FIG. 6, a diagram of the user's eye is shown including a first plane Agp 600 according to the preferred embodiment of the present invention. Plane Agp 600 includes (on-axis) first light source 406 and first camera 402 focal center, the image of first glint 508 in image plane 518 (point g), and the image of pupil center 506 in image plane 518 (point p). Points C, G, g, and A are collinear. Points C, P, and P' are collinear. Points A, p, and P are collinear. The plane Agp spanning lines CGA and CPP' would therefore include lines PG and line AP'. Plane Agp 600 can be considered to be plane ABC (which also includes points H and h) rotated around line CGA by a measurable angle α. Line L 602 is the intersection between plane Agp and the screen plane. Hence the gaze vector intersects with the display screen plane at point P' on line L. Determination of line L alone may be of particular utility, depending on the application that uses gaze information. For example, the intersection of line L with a scroll bar can determine the position of the scroll bar slider, assuming that the user is looking at the scroll bar at a specific time. Determination of partial gaze information, e.g. line L, is an object of this invention.

Figure 7:
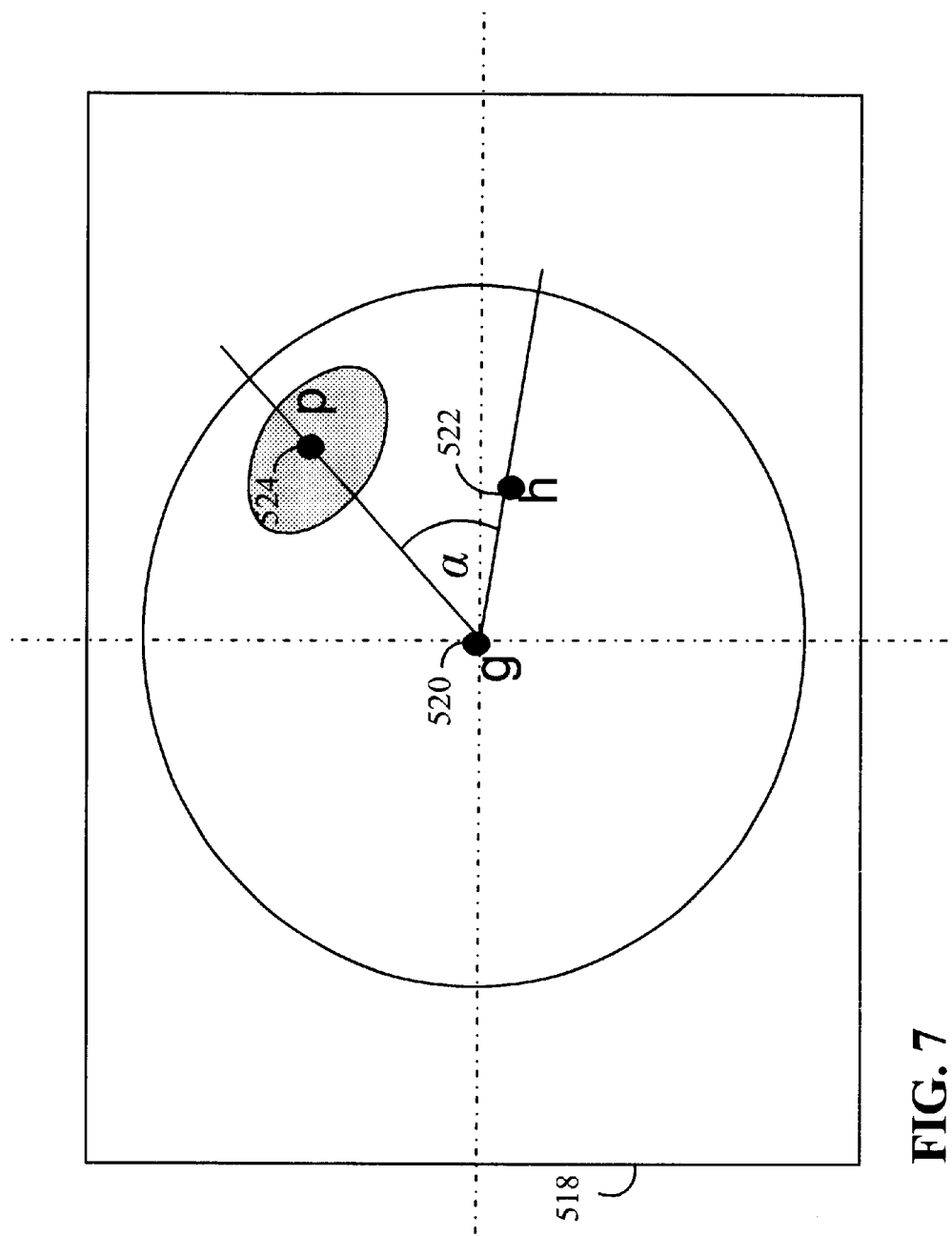
FIG. 7 is a view of the user's eye as seen by the first camera according to the preferred embodiment of the present invention.

Referring now to FIG. 7, a view of the user's eye as seen by first camera 402 is shown according to the preferred embodiment of the present invention. The identities and locations in the image plane of first camera 402 of projected first glint 508 (at point g) and projected second glint 510 (at point h) are determined from analysis of the images taken by first camera 402 when first light source 406 and second light source 408 were energized, preferably in an alternating manner as described above. In other words, the image of first glint 508 is due to first light source 406, and the image of second glint 510 is due to second light source 408, so if the light sources are alternately energized only one glint will appear in each interlaced scan made by first camera 402. Projected pupil center 506 (at point p) is also identified and located, preferably from the difference image generated by subtraction of even and odd interlaced scans and subsequent processing via conventional image analysis techniques. Angle α separating plane ABC and Agp 600 is therefore merely the angle pgh between line gh and line gp in this Figure, which is a view along the axis of plane rotation.

Alternately, line gp can be determined without estimating an exact point defining pupil center 506 location in image plane 518. Line gp can be a line that extends from the glint image through the pupil image to maximize the symmetry of the pupil image. If the portion of the pupil image on one side of line gp were "folded over" line gp onto the other portion of the pupil image, the overall differential pupil area would be minimized. Alternately, line gp can be chosen to go through the "center of mass" of the pupil image, i.e. a homogeneous slab of material shaped like the pupil image and of uniform thickness would balance if suspended on line gp. The pupil image will not be circular nor even elliptical if there are distortions in the corneal lens. However, it can be shown that when modeling the eye as a corneal lens attached to a spherical ball, the line of sight must lie on the plane passing through the glint and the symmetry line of the pupil as imaged via perspective projection onto a camera's image plane. Under this model, the line of sight may not pass through the measured pupil center due to the distortion the corneal lens induces on the pupil image.

Figure 8:
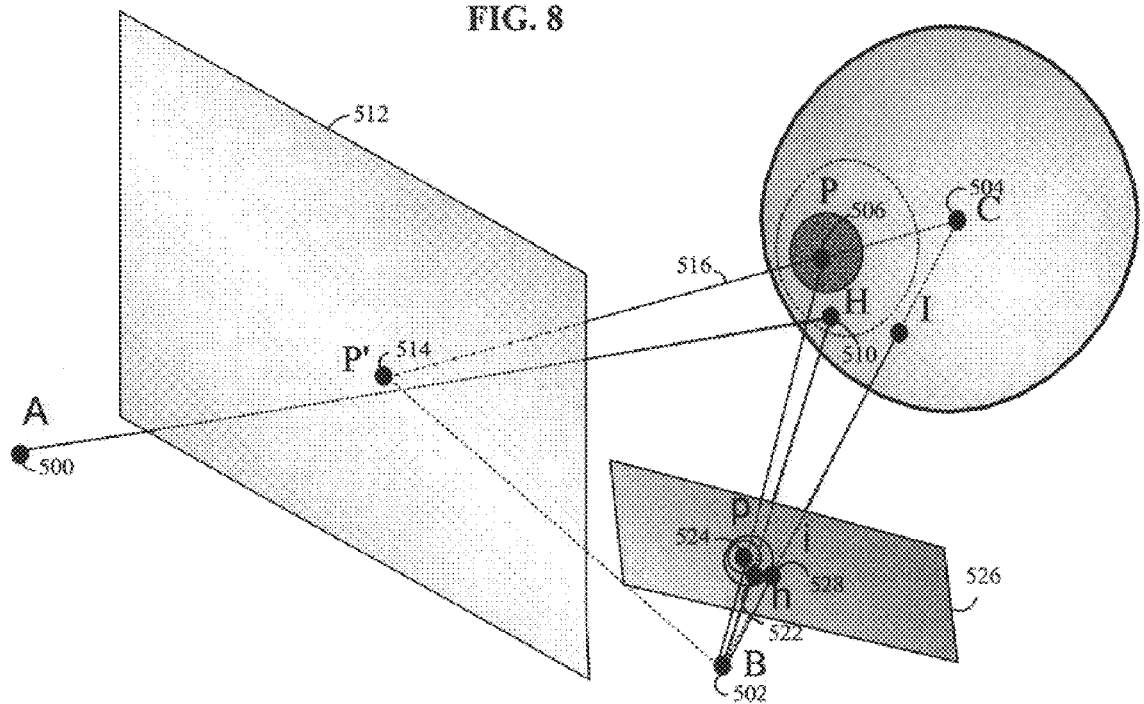
FIG. 8 is a diagram of the user's eye according to the preferred embodiment of the present invention.

Referring now to FIG. 8, a diagram of the user's eye is shown in accordance with the preferred embodiment of the present invention. This Figure is similar to FIG. 5, but describes the view of the user's eye as seen by second camera 404. Light from second light source 408 reflects from the user's cornea at point I back to second camera 404, producing second glint 510 in the image plane 526 of second camera 404. Light emitted from first light source 406 reflects from the user's cornea at point H and is visible by second camera 404 as first glint 508. Points H and I lie on plane ABC. Second image plane 526 is a plane orthogonal to the optical axis of second camera 402. Point i 528 is the image of second glint 510 in image plane 526. Point h 522 is the image of first glint 508 in image plane 526. Point p 524 is the image of pupil center 506 in image plane 526.

Figure 9:
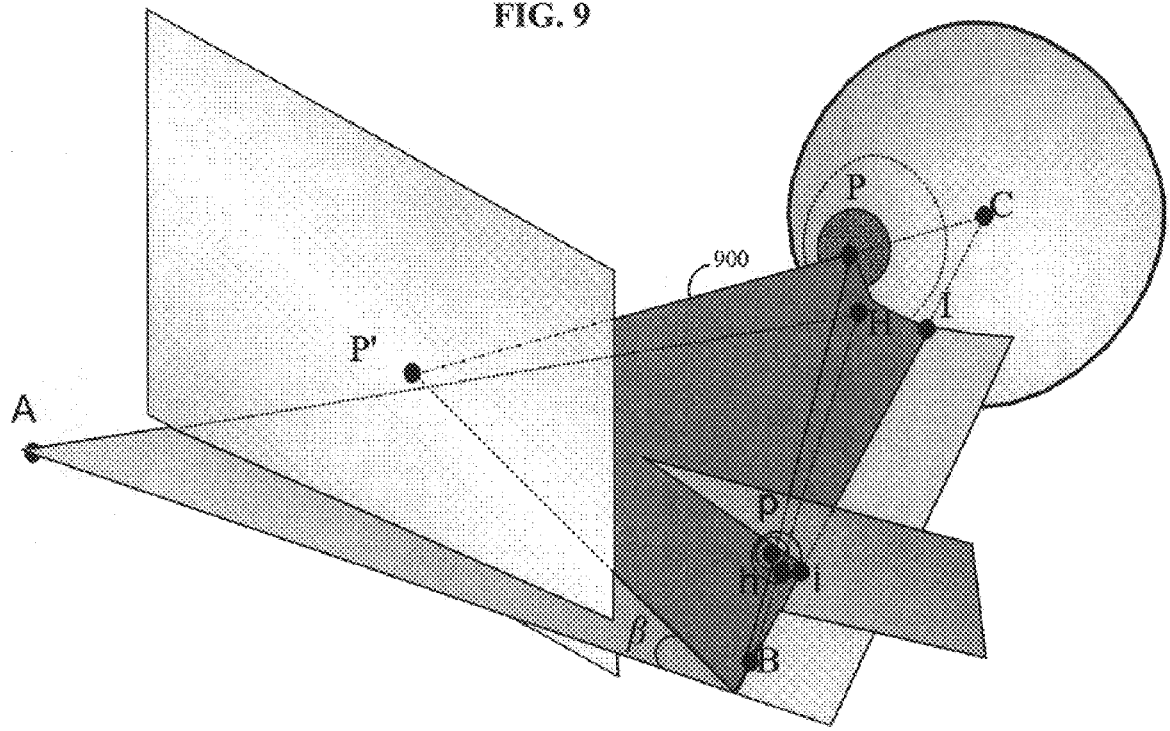
FIG. 9 is a diagram of the user's eye including a second plane Bip containing the gaze vector according to the preferred embodiment of the present invention.

Referring now to FIG. 9, a diagram of the user's eye is shown including a second plane Bip 900 according to the preferred embodiment of the present invention. Plane Bip 900 includes second light source 408 and second camera 404, second glint 510 in image plane 522, and pupil center 506. Points C, I, and B are collinear. Points C, P, and P' are collinear. A plane spanning lines CIB and CPP' would therefore include lines PI and line BP'. Plane Bip 900 can be considered to be plane ABC (which is also plane ABH) rotated around line CIB by a particular angle β.

Figure 10:
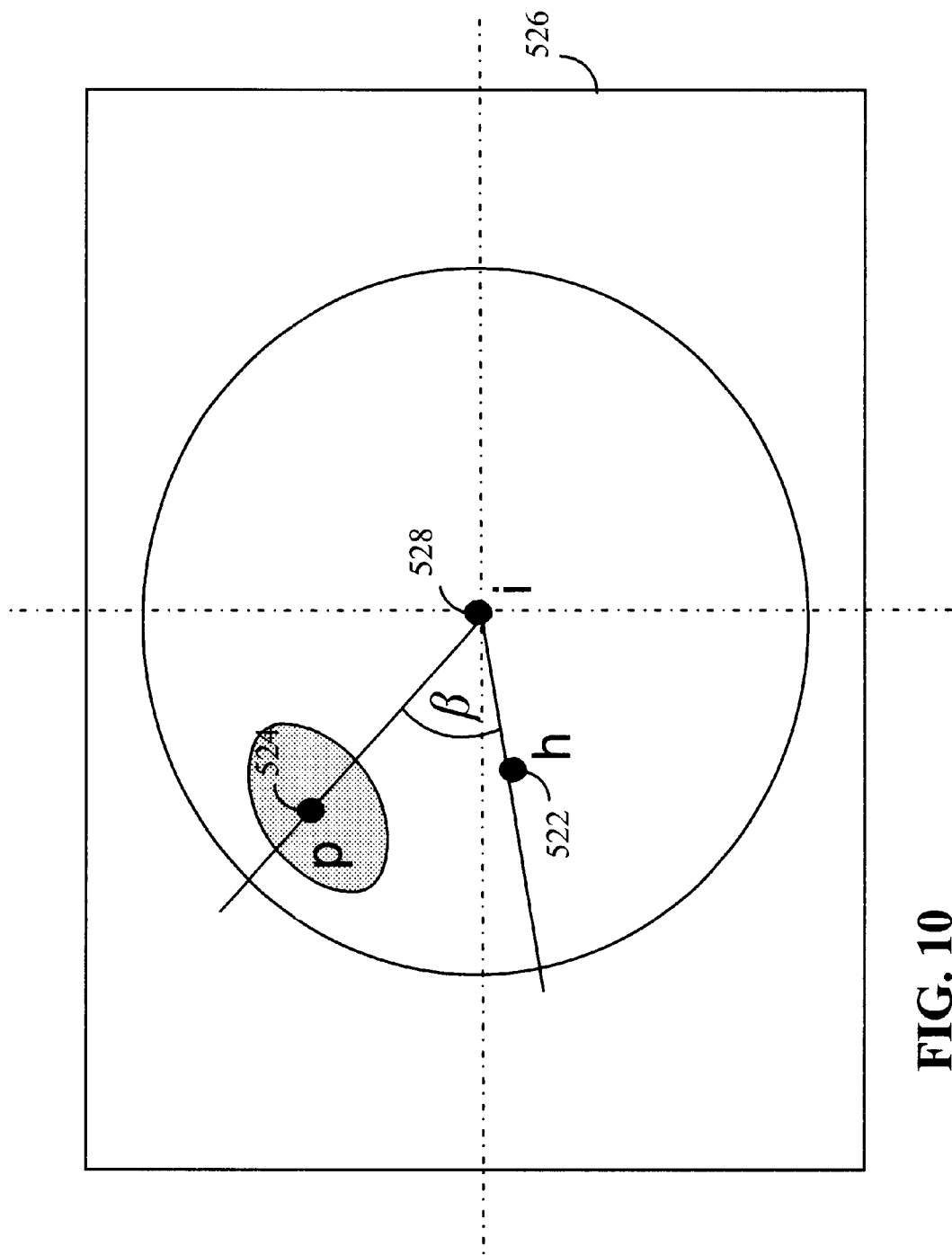
FIG. 10 is a view of the user's eye as seen by the second camera according to the preferred embodiment of the present invention.

Referring now to FIG. 10, a view of the user's eye as seen by second camera 404 is shown according to the preferred embodiment of the present invention. The identities and locations in the image plane 526 of second camera 404 of first glint 508 (at point h) and second glint 510 (at point i) are determined from analysis of the images taken by second camera 402 when first light source 406 and second light source 408 were energized, preferably in an alternating manner as described above. In other words, first glint 508 is due to first light source 406, and second glint 510 is due to second light source 408, so if the light sources are alternately energized only one glint will appear in each interlaced scan made by second camera 404. Pupil center 506 (at point p) is also identified and located in image plane 526, preferably from the difference image generated by subtraction of interlaced scan rows and subsequent processing techniques as described above. Angle β separating plane ABC and Bip 900 is therefore merely the angle hip between line ih and line ip in this Figure, which is a view along the axis of plane rotation.

Figure 11:
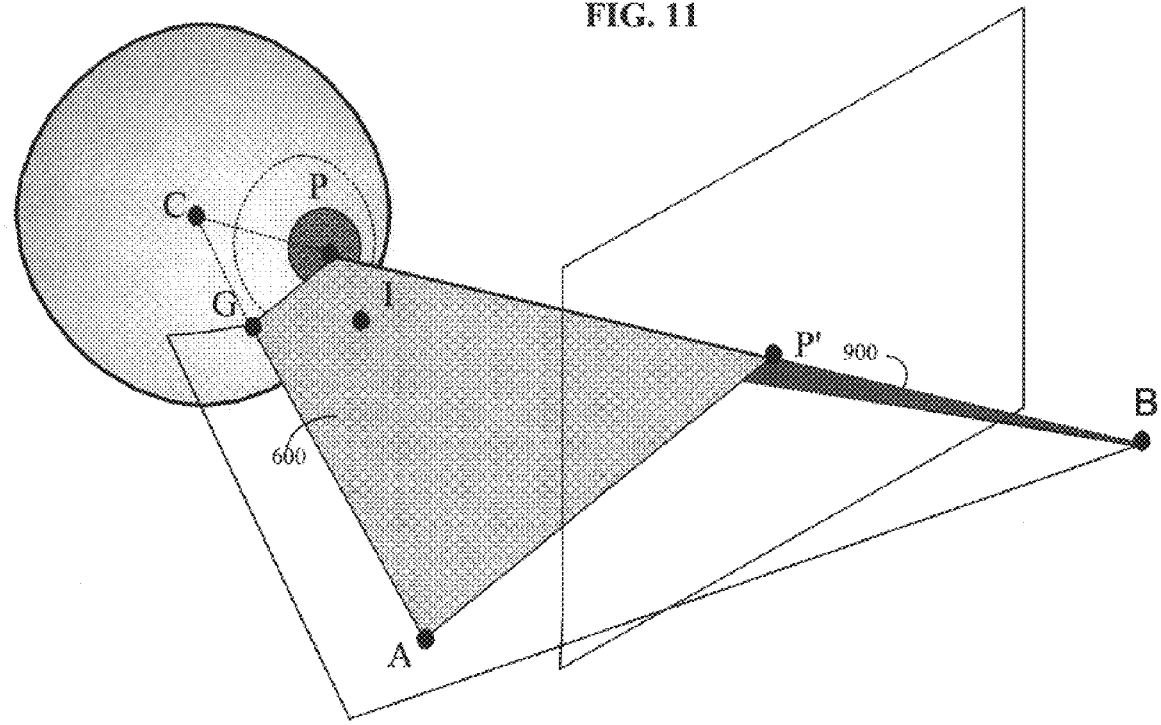
FIG. 11 is a diagram of the user's eye including a gaze vector defined by the intersection of the first plane and the second plane, and a point of regard, according to the preferred embodiment of the present invention.

Referring now to FIG. 11, a diagram of a user's eye including first plane Agp 600 and second plane Bip 900 is shown according to the preferred embodiment of the present invention. Line CPP' is the intersection of first plane Agp 600 and second plane Bip 900. Note that point C, center of cornea curvature 504, need not be explicitly computed to determine either gaze vector 516 or point of regard P' 514; point C can be indirectly determined if needed. The intersection of line CP (gaze vector 516) with the pre-defined display screen 512 plane (or another observed object, whether planar or not) is point of regard P' 514. Point P' 514 is known because the relative position of first camera 402 and second camera 404 to display screen 512 plane and to each other is known, and the relative positions of first glint 508 and second glint 510 and pupil center 506 in image planes 518 and 526 are known.

In the above analysis, it is assumed that the eye is a sphere (a good first approximation). However, more detailed analysis shows that it is enough to assume that the eye has rotational symmetry around the axis connecting the pupil center and the eyeball center. This is a good approximation except for the case of large astigmatism. The invention therefore tracks eye gaze properly for near-sighted and far-sighted users. While the invention has been described in a preferred embodiment employing two cameras, embodiments using more than two cameras are also included within the scope of the invention. Similarly, embodiments in which both of the user's eyes are tracked, each by at least one camera, is included within the scope of the invention.

Figure 12:
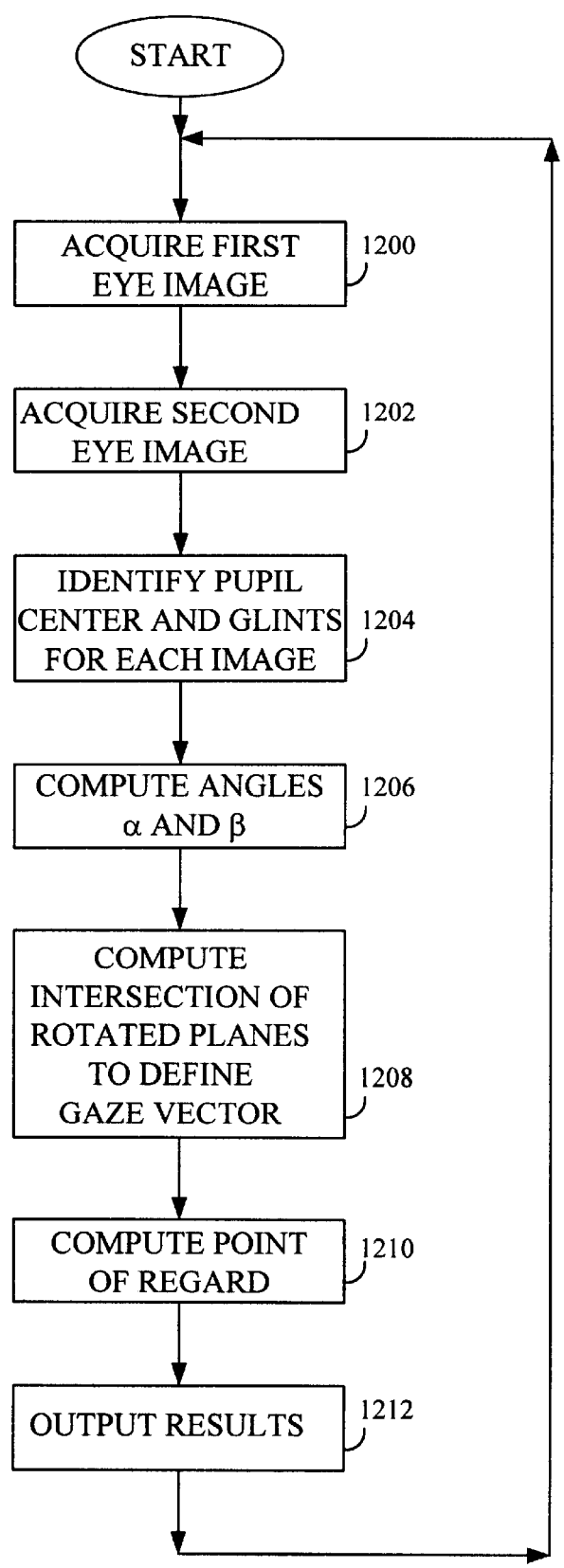
FIG. 12 is a flowchart of the eye gaze tracking method according to the preferred embodiment of the present invention.

Referring now to FIG. 12, a flowchart of the eye gaze tracking method is shown according to the preferred embodiment of the present invention. In step 1200, first camera 402 generates an image of the user's eye. In step 1202, second camera 404 generates an image of the user's eye. Each image may include interlaced scans and is passed to computer 400 as described above. In step 1204, for each image, computer 400 identifies and locates pupil center 506 and first glint 508 and second glint 510 in the image planes. In step 1206, computer 400 computes the plane rotation angles α and β. In step 1208, computer 400 identifies gaze vector 516 as the intersection line of first plane 600 and second plane 900. In step 1210, computer 400 identifies point of regard 514 from gaze vector 516 and data describing the spatial arrangement of first camera 402, second camera 404, and display screen 512 plane (or another observed object, whether planar or not). In step 1212, computer 400 generates outputs describing gaze vector 516 and point of regard 514 and begins another cycle of the method.

Figure 13:
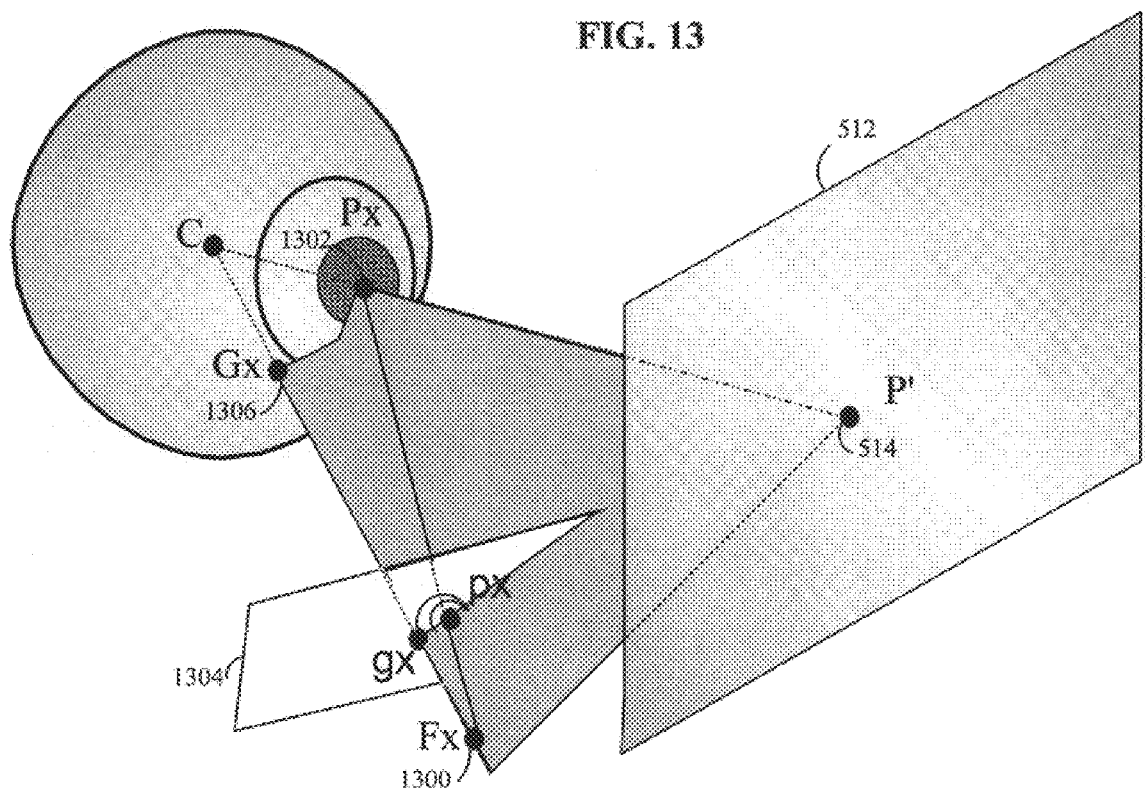
FIG. 13 is a diagram of a second embodiment of the present invention.

Referring now to FIG. 13, a diagram of a user's eye according to a second embodiment of the present invention is shown. The second embodiment is identical to the preferred embodiment, except that each of the two intersecting planes are computed from different data points. In this embodiment, it is not necessary for either camera to view reflected light originally emitted by a light source other than its own, although this additional data can be used. However, unlike the preferred embodiment, it is necessary in this second embodiment for the roll angle for each camera to be known, i.e. some "up vector" or absolute orientation reference is needed. For each camera, the focal center Fx of the camera 1300, the position of the pupil center Px 1302 as projected onto the image plane 1304 of the camera, and the position of the glint Gx 1306 produced by that camera's own light source projected onto the image plane 1304 of the camera define a plane FxPxGx. The intersection of the first plane with display screen plane 512 defines a first line containing point of regard 514. The intersection of the second plane with display screen plane 512 defines a second line containing point of regard 514. The gaze vector 516 is a line defined by the intersection between the first plane and the second plane and extending from the user's eye toward an observed object. The point of regard 514 is computed from the intersection of gaze vector 516 with the observed object, which corresponds to the intersection of the first line and the second line when the observed object is planar. While the invention has been described in a second embodiment employing two cameras, embodiments using more than two cameras are also included within the scope of the invention. Similarly, an embodiment employing two cameras, each of which tracks a different user eye, is also included within the scope of the invention.

Figure 14:
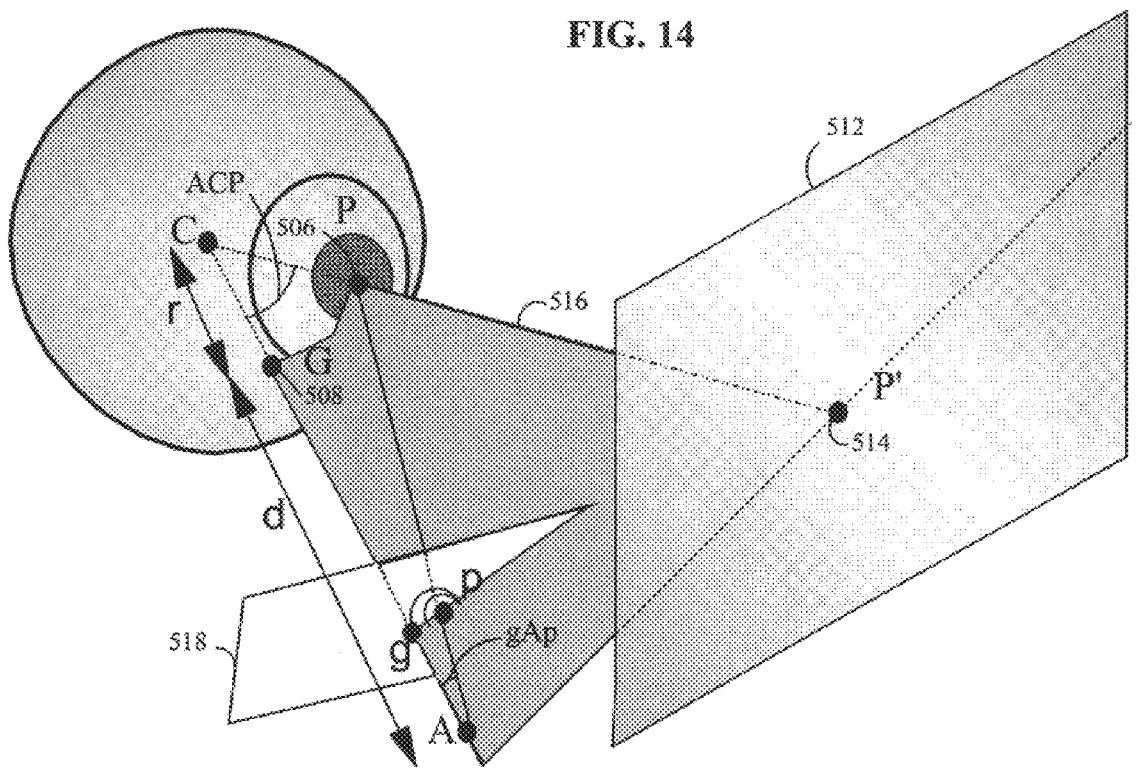
FIG. 14 is a diagram of a third embodiment of the present invention.

Referring now to FIG. 14, a diagram of a third embodiment of the present invention is shown. This embodiment requires a one-time calibration of the radius of curvature of the user's cornea, and an estimate of the distance of the eye from display screen 512 plane or camera 402. The third embodiment system components are identical to those of the second embodiment except that the third embodiment omits second camera 404, second light source 408 and second frame grabber 414. Projections of first glint 508 (at point g) and pupil center 506 (at point p) are identified and located in image plane 518, and the distance between points g and p is measured. If the user is looking directly at camera 402, there will be no distance between points p and g, i.e. they will coincide. Angle gAp and the distance d from the camera 402 are used to compute distance PG, which is the actual distance between pupil center 506 and glint 508 on the eye. Because the radius of corneal curvature r is known, the angle ACP' can be computed from distance PG via elementary trigonometry. Point of regard 514 and the gaze vector 516 are computed from the position of camera 402. Camera 402 may alternately scan each of the user's eyes to allow two computations as described above, reducing the need for the distance d.

A general purpose computer is programmed according to the inventive steps herein. The invention can also be embodied as an article of manufacture—a machine component—that is used by a digital processing apparatus to execute the present logic. This invention is realized in a critical machine component that causes a digital processing apparatus to perform the inventive method steps herein. The invention may be embodied by a computer program that is executed by a processor within a computer as a series of computer-executable instructions. These instructions may reside, for example, in RAM of a computer or on a hard drive or optical drive of the computer, or the instructions may be stored on a DASD array, magnetic tape, electronic read-only memory, or other appropriate data storage device.

While the invention has been described with respect to illustrative embodiments thereof, it will be understood that various changes may be made in the apparatus and means herein described without departing from the scope and teaching of the invention. Accordingly, the described embodiment is to be considered merely exemplary and the invention is not to be limited except as specified in the attached claims.

We claim:

1. A method for eye gaze tracking, comprising the steps of:
   focusing at least one camera upon at least one of a user's eyes, each said camera having a focal center, an image plane, and a co-located light source emitting light toward said eye;
   identifying and locating image aspects including at least one glint and a pupil image in said image plane; and
   computing a gaze vector from at least one plane generated from said image aspects and camera position and orientation data.

2. The method of claim 1 wherein said method is adapted for use with an animal.

3. The method of claim 1 wherein said method is adapted for use with a person.

4. The method of claim 1 wherein said method is adapted for use with a baby.

5. The method of claim 1 comprising the further step of locating a point of regard as the intersection of said gaze vector with a predetermined surface.

6. A method for eye gaze tracking, comprising the steps of:
   focusing at least one camera upon at least one of a user's eyes, each said camera having a focal center, an image plane, and a co-located light source emitting light toward said eye;
   identifying and locating image aspects including at least one glint and a pupil image in said image plane;
   computing a gaze vector from at least one plane generated from said image aspects and camera position and orientation data;
   synchronizing scanning signals controlling each one of said at least one cameras; and
   responsively alternately energizing said light sources to identify correspondences between said light sources and said glints.

7. The method of claim 1 comprising the further step of correcting said gaze vector for a foveal axis offset angle.

8. A method for eye gaze tracking, comprising the steps of:
   focusing at least one camera upon at least one of a user's eyes, each said camera having a focal center, an image plane, and a co-located light source emitting light toward said eye;
   identifying and locating image aspects including at least one glint and a pupil image in said image plane;
   computing a gaze vector from at least one plane generated from said image aspects and camera position and orientation data;
   determining an angle between said glint in said image plane, said focal center, and a center of said pupil image in said image plane;
   finding a separation on said eye between said glint and said pupil center using said angle and a distance estimate between said eye and a point of regard;
   defining a second angle between said focal center, a corneal curvature center, and said pupil center using a radius of corneal curvature to define said gaze vector; and
   locating said point of regard at the intersection of said gaze vector with a predetermined surface.

9. A method for eye gaze tracking, comprising the steps of:
   focusing at least one camera upon at least one of a user's eyes, each said camera having a focal center, an image plane, and a co-located light source emitting light toward said eye;
   identifying and locating image aspects including at least one glint and a pupil image in said image plane;
   computing a gaze vector from at least one plane generated from said image aspects and camera position and orientation data;
   defining for each one of a plurality of said at least one cameras a particular plane spanning said glint in said image plane, said focal center, and a center of said pupil image in said image plane; and
   identifying an intersection line of said particular planes as said gaze vector.

10. A method for eye gaze tracking, comprising the steps of:
    focusing at least one camera upon at least one of a user's eyes, each said camera having a focal center, an image plane, and a co-located light source emitting light toward said eye;
    identifying and locating image aspects including at least one glint and a pupil image in said image plane;
    computing a gaze vector from at least one plane generated from said image aspects and camera position and orientation data;
    for each one of a plurality of said at least one cameras, defining in said image plane an angle spanning a center of said pupil image, a first glint, and a second glint, wherein said first glint results from said light source on each said one camera and said second glint results from another light source;
    defining a base plane spanning said focal center for each said one camera and said focal center for each other camera in said plurality and a point on said eye corresponding to said second glint;
    for each one of said at least one cameras in said plurality, defining a particular plane by rotating said base plane through each said corresponding angle around an axis including said focal center for each said one camera and said first glint; and
    identifying a line at an intersection of said planes as said gaze vector.

11. The method of claim 10 wherein said center of said pupil image lies on a line maximizing symmetry of said pupil image.

12. A method for eye gaze tracking, comprising the steps of:
    focusing at least one camera upon at least one of a user's eyes, each said camera having a focal center, an image plane, and a co-located light source emitting light toward said eye;

identifying and locating image aspects including at least one glint and a pupil image in said image plane; and computing a line containing a point of regard on a display screen from said image aspects and camera position and orientation data.

13. The method of claim 12 wherein a position of said line on said display screen controls a graphical user interface element.

14. The method of 13 wherein said graphical user interface element is a scroll bar slider.

15. A system for eye gaze tracking, comprising:

at least one camera focusing upon at least one of a user's eyes, each said camera having a focal center, an image plane, and a co-located light source emitting light toward said eye; and a computer to identify and locate image aspects including at least one glint and a pupil image in said image plane, and to compute a gaze vector from at least one plane generated from said image aspects and camera position and orientation data.

16. The system of claim 15 wherein said system is adapted for use with an animal.

17. The system of claim 15 wherein said system is adapted for use with a person.

18. The system of claim 15 wherein said system is adapted for use with a baby.

19. The system of claim 15 wherein said computer locates a point of regard as the intersection of said gaze vector with a predetermined surface.

20. A system for eye gaze tracking, comprising:

at least one camera focusing upon at least one of a user's eyes, each said camera having a focal center, an image plane, and a co-located light source emitting light toward said eye;

a computer to identify and locate image aspects including at least one glint and a pupil image in said image plane, and to compute a gaze vector from at least one plane generated from said image aspects and camera position and orientation data; and a source for synchronous scan signals controlling each one of said at least one cameras and alternately energizing said light sources to identify correspondences between said light sources and said glints.

21. The system of claim 15 wherein said computer corrects said gaze vector for a foveal offset axis angle.

22. A system for eye gaze tracking, comprising:

at least one camera focusing upon at least one of a user's eyes, each said camera having a focal center, an image plane, and a co-located light source emitting light toward said eye; and a computer to identify and locate image aspects including at least one glint and a pupil image in said image plane, and to compute a gaze vector from at least one plane generated from said image aspects and camera position and orientation data, wherein said computer (1) determines an angle between said glint in said image plane, said focal center, and a center of said pupil image in said image plane;

(2) finds a separation on said eye between said glint and said pupil center using said angle and a distance estimate between said eye and a point of regard;

(3) defines a second angle between said focal center, a corneal curvature center, and said pupil center using a radius of corneal curvature to define said gaze vector; and (4) locates said point of regard at the intersection of said gaze vector with a predetermined surface.

23. A system for eye gaze tracking, comprising:

at least one camera focusing upon at least one of a user's eyes, each said camera having a focal center, an image plane, and a co-located light source emitting light toward said eye; and a computer to identify and locate image aspects including at least one glint and a pupil image in said image plane, and to compute a gaze vector from at least one plane generated from said image aspects and camera position and orientation data, wherein said computer (1) defines for each one of a plurality of said at least one cameras a particular plane spanning said glint in said image plane, said focal center, and a center of said pupil image in said image plane; and (2) identifies an intersection line of said planes as said gaze vector.

24. A system for eye gaze tracking, comprising:

at least one camera focusing upon at least one of a user's eyes, each said camera having a focal center, an image plane, and a co-located light source emitting light toward said eye; and a computer to identify and locate image aspects including at least one glint and a pupil image in said image plane, and to compute a gaze vector from at least one plane generated from said image aspects and camera position and orientation data, wherein said computer (1) for each one of a plurality of said at least one cameras, defines in said image plane an angle spanning a center of said pupil image, a first glint, and a second glint, wherein said first glint results from said light source on each said one camera and said second glint results from another light source;

(2) defines a base plane spanning said focal centers for each said one camera and said focal center for each other camera in said plurality and a point on said eye corresponding to said second glint;

(3) for each one of said at least one cameras in said plurality, defines a particular plane by rotating said base plane through each said corresponding angle around an axis including said focal center for each said one camera and said first glint; and (4) identifies a line at an intersection of said planes as said gaze vector.

25. The system of claim 24 wherein said computer chooses said center of said pupil image to lie on a line maximizing symmetry of said pupil image.

26. A system for eye gaze tracking comprising:

at least one camera focused upon at least one of a user's eyes, each said camera having a focal center, an image plane, and a co-located light source emitting light toward said eye; and a computer to identify and locate image aspects including at least one glint and a pupil image in said image plane, and to compute a line containing a point of regard on a display screen from said image aspects and camera position and orientation data.

27. The system of claim 26 wherein a position of said line on said display screen controls a graphical user interface element.

28. The system of 27 wherein said graphical user interface element is a scroll bar slider.

29. A system for eye gaze tracking comprising:

means for focusing at least one camera upon a user's eye, each said camera having a focal center, an image plane, and a co-located light source emitting light toward said eye;

means for identifying and locating, in an image plane, image aspects including at least one glint and a pupil image;

means for computing a gaze vector from at least one plane generated from said image aspects; and means for determining a point of regard from said image aspects and camera position and orientation data.

30. A computer program product including a program storage device readable by a machine, tangibly embodying a program of instructions executable by the machine to perform method steps for eye gaze tracking, said method steps comprising:

focusing at least one camera upon a user's eye, each said camera having a focal center, an image plane, and a co-located light source emitting light toward said eye;

identifying and locating, in an image plane, image aspects including at least one glint and a pupil image;

computing a gaze vector from at least one plane generated from said image aspects; and determining a point of regard from said image aspects and camera position and orientation data.

* * * * *